United States Patent [19]

Koskimies et al.

[11] Patent Number: 4,801,758

[45] Date of Patent: Jan. 31, 1989

[54] PROCEDURE FOR PRODUCING HYDROQUINONE

[75] Inventors: Salme Koskimies, Helsinki; Taru Haimala, Mäntsälä, both of Finland

[73] Assignee: Neste Oy, Finland

[21] Appl. No.: 51,736

[22] Filed: May 18, 1987

[51] Int. Cl.[4] .............................................. C07C 39/10
[52] U.S. Cl. ...................................... 568/768; 568/771
[58] Field of Search ............... 568/563, 768, 771, 569, 568/577, 576

[56] References Cited

U.S. PATENT DOCUMENTS

| | | | |
|---|---|---|---|
| 2,784,238 | 3/1957 | Hutchinson | 568/768 |
| 3,978,142 | 8/1976 | Burkholder | 568/569 |
| 4,271,321 | 6/1981 | Voges | 568/577 |
| 4,273,623 | 6/1981 | Hashimoto et al. | 568/768 |
| 4,328,377 | 5/1982 | Mori et al. | 568/768 |
| 4,463,198 | 7/1984 | Nowak et al. | 568/768 |
| 4,670,609 | 6/1987 | Bennett | 568/768 |

FOREIGN PATENT DOCUMENTS

| | | | |
|---|---|---|---|
| 2036937 | 1/1972 | Fed. Rep. of Germany | 568/576 |
| 2421039 | 11/1974 | Fed. Rep. of Germany | 568/576 |

Primary Examiner—Warren B. Lone
Attorney, Agent, or Firm—Steinberg & Raskin

[57] ABSTRACT

A procedure for producing hydroquinone from a hydrocarbon mixture obtained as a by-product when producing cumene, by selectively oxidizing tertiary alkylaromatics to form hydroperoxides, by separating the dihydroperoxide of p-diisopropylbenzene from the oxidation product by selective crystallization through cooling, and by decomposing the dihydroperoxide of p-diisopropylbenzene with the aid of an acid catalyst to form the hydroquinone.

26 Claims, No Drawings

PROCEDURE FOR PRODUCING HYDROQUINONE

BACKGROUND OF THE INVENTION

The present invention concerns a procedure for producing hydroquinone by oxidizing a starting material mixture comprising a component containing tertiary alkylaromatic and a component containing hydroperoxides produced in the oxidizing reaction of the alkylaromatics. The mixture is selectively oxidized with the aid of oxygen at a temperature from about 60° to 180° C., with dihydroperoxide of p-diisopropylbenzene then being separated from the mixture and decomposed by acid catalysis at about 20°–150° C. to form hydroquinone. The invention also relates to producing the dihydroperoxide of p-diisopropylbenzene and separating the same from the reaction mixture.

It is known in the art that aliphatic hydrocarbons such as isobutane, 2-methylbutane, decahydronaphthalene, and alkyl aromatics such as cumene, methylnaphthalene, diisopropylbenzene, etc. can be oxidized with the aid of oxygen to form equivalent hydroperoxides so that either the tertiary or α-aromatic carbon reacts. It is also known in the art that these hydroperoxides react under the effect of acid catalysts to produce the corresponding phenol or alcohol, and aldehyde or ketone.

As known in the art, such a procedure has been used, for instance, in producing phenol from cumene, cresols from cymene, or resorcinol from m-diisopropylbenzene, and hydroquinone from p-diisopropylbenzene. In the prior art procedures, resorcinol and hydroquinone have been produced using pure, relatively expensive m- or p-diisopropylbenzenes as starting materials.

SUMMARY OF THE INVENTION

Accordingly, it is an object of the present invention to provide a new and improved synthesis of hydroquinone, and to provide a new and improved synthesis of dihydroperoxide of p-diisopropylbenzene used to produce the hydroquinone.

It is also an object of the present invention to provide for selective synthesis of the hydroquinone from a hydrocarbon mixture obtained as a by-product when producing cumene.

It is another object of the present invention to avoid the need for purifying intermediates in the production of hydroquinone.

It is a further object of the present invention to avoid unnecessary steps, e.g. a neutralizing step, in the production of hydroquinone.

These and other objects are attained by the present invention which is directed to a method of producing hydroquinone which comprises oxidizing a mixture of tertiary alkylaromatics and hydroperoxides thereof to form hydroperoxides of the tertiary alkylaromatics including dihydroperoxide of p-diisopropylbenzene, cooling the thus-formed hydroperoxides of the tertiary alkylaromatics whereby the dihydroperoxide of p-diisopropylbenzene crystallizes, and separating the dihydroperoxide of p-diisopropylbenzene from the remaining components and decomposing the same by acid catalysis to form hydroquinone. More particularly, the present invention is directed to producing the hydroquinone by oxidizing a mixture of about 10–80% by weight of diisopropylbenzenes and about 20–90% by weight of $C_4$–$C_9$ alkylbenzenes to form the reaction mixture containing the dihydroperoxide of p-diisopropylbenzene, which is then cooled so that the di-hydroperoxide of p-diisopropylbenzene crystallizes and the remaining components can be returned for oxidization (the di-hydroperoxide of p-diisopropylbenzene is separated and decomposed by acid catalysis to form hydroquinone).

The present invention is also directed to a method of producing the dihydroperoxide of p-diisopropylbenzene by oxiding the mixture of about 10–80% by weight of diisopropylbenzenes and about 20–90% by weight of $C_4$–$C_9$ alkylbenzenes, to form the reaction mixture containing the di-hydroperoxide of p-diisopropylbenzene, and cooling the thus-formed reaction mixture, whereby the dihydroperoxide of p-diisopropylbenzene crystallizes and the remaining components can be returned for oxidation.

Accordingly, the procedure of the present invention for producing hydroquinone from a hydrocarbon mixture obtained as a by-product of cumene, is characterized by using for the component containing tertiary alkylaromatics, a product obtained as a by-product in producing cumene which has a boiling range of about 170°–220° C. and which contains from about 10 to 80% by weight of diisopropylbenzenes and from about 20 to 90% by weight, preferably about 20 to 60% by weight of a mixture of $C_4$–$C_9$ alkylbenzenes. After oxidation of the reaction mixture containing the component of the tertiary alkylaromatics, the di-hydroperoxide of p-diisopropylbenzene will selectively crystallize out by cooling the reaction mixture. The dihydroperoxide of p-diisopropylbenzene is then separated and decomposed by acid catalysis to form hydroquinone and acetone, while the remaining components, e.g. monohydroperoxides and dihydroperoxide of m-diisopropylbenzene, remain in the oxidizing solution and are returned to the oxidation reactor.

DESCRIPTION OF THE PREFERRED EMBODIMENTS

The methods of the present invention are based on the observation that in the oxygen oxidizing process, reactivities of different alkylaromatics and solubilities of the oxidation products thereof which are obtained, are all different.

This has further opened up the possibility that alkylaromatic mixtures may also be used for starting material, with it then being possible to optimize reaction conditions so that only certain compounds in the first place are oxidized, i.e. tertiary aralkyl compounds. Additionally, if a hydrocarbon mixture obtained as a by-product when producing cumene is used for the starting material, the oxidation products which are obtained differ so much in solubility from the mother solution, that the dihydroperoxide of p-diisopropylbenzene can be selectively separated from the other oxidation products directly by crystallizing, with hydroquinone being further obtained by acid-catalytic decomposition of the same.

Acids known to be suitable for the acid catalysis include mineral acids, such as sulphuric acid, phosphoric acid, etc., acid aluminosilicates, sulphur trioxide, and Lewis acids such as borotrifluoride, aluminum trichloride, etc. However, solid ion exchange resin containing acid groups is preferably used for decomposing the dihydroperoxides in the procedure of the invention. The advantage is attained in that the extra neutralizing step is avoided, e.g. as compared to sulphuric acid, because the catalyst can be removed by filtering. Ketones such as acetone, methylethylketone, methylisobutylketone, and/or low-boiling aliphatic or aromatic hydrocarbons may be used for solvent in the decomposing step.

It is thus understood that the procedures of the present invention are based upon the different reactivities in oxygen oxidation of the alkyl aromatics present in the by-product mixture obtained when producing cumene, and in particular on the different solubility of dihydroperoxide of p-diisopropylbenzene from the solubilities of the other oxidation products in the mother solution. This has further enabled the reaction conditions to be optimized so that only certain compounds, in the first place tertiary aralkyl compounds, are oxidized and that of the oxidation products so produced, only dihydroperoxide of p-diisopropylbenzene is precipitated. Under these circumstances, the other hydrocarbon components in the reaction mixture act, in contrast, as an inert diluent. On one hand, these other components promote the separation in crystalline form of the dihydroperoxide of p-diisopropylbenzene that is formed. On the other hand, these other hydrocarbon components in the reaction mixture cause retardation of the oxidizing reaction, under the oxidizing conditions which are typical to pure diisopropylbenzene.

Using a temperature higher than normal, i.e. about 60°–180° C., more prefrably about 90°–130° C., and most preferably about 90°–100° C. in the oxidizing phase, the oxidizing may still be effected at a speed equivalent to that of the pure starting material components. Moreover, the number of by-products produced is then smaller in comparison with the oxidizing reaction carried out at a lower temperature.

It is known in the art that the oxygen oxidation process of diisopropylbenzenes progresses in a manner such that in the first step, corresponding monohydroperoxides are formed, and that the dihydroperoxides begin to form when the content of monhydroperoxides in the solution has been sufficiently elevated (over about 10%). It is moreover known in the art that the oxidation can be catalyzed by adding the corresponding dihydroperoxide to the starting material.

The component containing tertiary alkylaromatics contains about 10–80% by weight of diisopropylbenzenes and about 20–60% by weight of a mixture of alkylbenzenes, in particular t-butylbenzene, 1,1-dimethylpropylbenzene, i- and 1-hexylbenzenes, and 2- and 3-phenylhexanes.

Various hydroperoxides may also be used as catalysts in the procedures of the present invention. Recirculation of oxidized mother solution from which the dihydroperoxide of p-diisopropylbenzene has been removed, back to the oxidizing reactor, is highly useful with a view to producing dihydroperoxides. This is primarily due to the fact that the mother solution contains extraordinary quantities of monohydroperoxides of diisopropylbenzene and some m-diisopropylbenzene, which may further act as catalysts in the oxidizing reaction. It is endeavored to maintain the total hydroperoxide content in the (entire) oxygen oxidation process in the range from about 10 to 80% by weight, preferably in the range from about 20 to 60% by weight. The proportion of recirculated mother solution to the starting material may be about 0.01:1–10:1, preferably about 0.25:1–2:1, more preferably about 0.05:1–2:1.

A number of methods are known to exist for separating dihydroperoxides of diisopropylbenzene from the mother solution. The dihydroperoxides may, for instance, be extracted into a 4% aqueous NaOH solution, from which the dihydroperoxides may be further transferred into a methylisopropylketone solution for decomposing. Other procedures known in the art include the separation of the dihydroperoxides usung an ion exchange resin. containing basic groups, or crystallizing the dihydroperoxides from the mother solution either as sodium salts or by adding inert aliphatic or aromatic hydrocarbon to the mother solution.

In the procedures of the present invention, crystallization of dihydroperoxide of p-diisopropylbenzene in particular from the mother solution, is very much easier than in the normal oxidizing process of diisopropylbenzenes, because the starting material often already contains 50% hydrocarbons acting as inert agents. Furthermore, the procedures of the invention differ from the procedures of the prior art, in that dihydroperoxide of m-diisopropylbenzene which is also produced in the oxidizing step, does not crystallize in the applied circumstances and conditions. The procedures are therefore selective, in particular for separating dihydroperoxide of p-diisopropylbenzene. This further makes it possible to obtain hydroquinone on acid decomposition which contains no significant amounts of phenolic impurities.

The by-product produced in conjunction with the production of cumene, containing about 25% p-diisopropylbenzene, is oxidized at about 60°–180° C., more preferably at about 90°–130° C., and most preferably at about 90°–100° C. in the procedures of the present invention, so that the total hydroperoxide content will be about 10–80% by weight, preferably about 20–60% by weight. The dihydroperoxide of p-diisopropylbenzene that is formed is crystallized from the mother solution by cooling. The mother solution is recirculated to the oxidizing reactor so that its (recycle) proportion relative to the starting material will be about 0.01:1–10:1, preferably about 0.25:1–2:1, and more preferably about 0.05:1–2:1. The crystalline dihydroperoxide of p-diisopropylbenzene is dissolved in methylisobutylketone and decomposed with the acid catalyst, preferably an acid ion exchange resin, to form hydroquinone and acetone at about 20–150° C., preferably at about 20–120° C.

The present invention differs from the prior art procedures by particularly rendering it possible to produce hydroquinone selectively from hydrocarbon mixture obtained as a by-product when producing cumene. Such a hydrocarbon mixture is considerably more advantageous than pure p-diisopropylbenzene which is used as starting material in the procedures of the prior art. Since application of the invention procedures involves no purifying of the by-product obtained in cumene production, and since the intermediate product, i.e. the dihydroperoxide of p-diisopropylbenzene is separable simply by crystallizing from the rest of the oxidation products when applying the procedures of the present invention, production of hydroquinone which is free from other phenol components is attained. Furthermore, since acid ion exchange resin is used for the catalyst in the decomposing step in the procedure of the invention, an extra neutralizing step is obviated. Thus, the invention procedure is considered quite simple indeed.

The present invention will be described in greater detail in the following non-restrictive examples:

EXAMPLES 1-5

500 ml of a hydrocarbon by-product obtained in cumene production, and presented in Table 1 below, was added into a cylindrical oxidizing reactor (diameter 45 mm and height 450 mm) provided with a heating jacket, thermometer, oxygen dispersing tube and oxygen flow meter:

TABLE I

| Component | Content % by weight |
|---|---|
| Isopropylbenzene | 1.342 |
| Tertiary butylbenzene | 3.771 |
| Secondary butylbenzene | 0.9672 |
| 2-phenyl-3-methylbutane | 0.352 |
| 1,1-dimethylpropylbenzene | 2.608 |
| 1-methylbutylbenzene | 0.403 |
| 1,3-diisopropylbenzene | 21.379 |
| i-$C_6$—benzene | 7.606 |
| 1,4-diisopropylbenzene | 25.942 |
| 1,1-dimethylbutylbenzene | 8.647 |
| 1-$C_6$—benzene | 1.579 |
| 3-phenylhexane | 5.810 |
| 2-phenylhexane | 2.245 |
| $C_7$—benzene | 0.491 |
| $C_9$—benzene | 0.611 |

The hydrocarbon mixture was heated to 100° C. Then, oxygen was conducted into the reactor through the oxygen dispersing tube at a constant flow rate of 330 ml/min.

After oxidation was carried out for 12.5 hrs, the total peroxide content of the solution was 1.1%. The reaction product was diluted with starting material so that the total hydroperoxide content in the mixture became 0.5%. This mixture was oxidized for 24.5 hrs, so that the total hydroperoxide content became 14.4%.

The oxidation products were as presented in Table II below, in the case where the proportion of hydroperoxide catalyst in the starting material was 0.9 or 4.5 percent by weight, with the reaction temperature 100° C.

TABLE II

| Example | Oxidizing time hours | Hydroperoxides percent at beginning | Hydroperoxides percent at end | m-MHP (a) % | p-MHP (a) % | m-DHP (b) % | p-DHP (b) % | m-HHP (c) % | p-HHP (c) % |
|---|---|---|---|---|---|---|---|---|---|
| 1 (d) | 12.5 | — | 1.1 | | | | | | |
| 2 (d) | 24.5 | 0.5 | 14.4 | | | | | | |
| 3 (d) | 26.0 | 0.9 | 20.0 | 5.3 | 9.4 | 1.9 | 0.9 | | |
| 4 (d) | 22.0 | 4.5 | 35.8 | 6.4 | 12.8 | 2.5 | 2.3 | 2.7 | 4.5 |
| 5 (e) | 40.0 | 1.3 | 8.5 | | | | | | |

(a) MHP = monohydroperoxide of diisopropylbenzene
(b) DHP = dihydroperoxide of diisopropylbenzene
(c) HHP = hydroxyhydroperoxide of diisopropylbenzene
(d) Oxidizing temperature 100° C.
(e) Oxidizing temperature 90° C.

EXAMPLES 6-10

A hydrocarbon mixture having the composition presented in Table I, was oxidized with oxygen in the manner described in Examples 1-5 at 110° C. Partially oxidized mother solution was used for catalyzing the oxidizing reaction, the mother solution being so recirculated that the total hydroperoxide content in the starting material was 0.9, 2.4, 4.9, 7.6% and 5.1, respectively in these examples. The resulting oxidation products formed are listed in Table III:

TABLE III

| Example | Oxidizing time hours | Hydroperoxides percent at beginning | Hydroperoxides percent at end | m-MHP (a) % | p-MHP (a) % | m-DHP (b) % | p-DHP (b) % | m-HHP (c) % | p-HHP (c) % |
|---|---|---|---|---|---|---|---|---|---|
| 6 | 10.5 | 0.9 | 19.9 | | | | | | |
| 7 | 8.5 | 2.4 | 19.8 | | | | | | |
| 8 | 9.0 | 4.9 | 34.0 | 3.7 | 7.5 | 5.8 | 3.8 | 2.3 | 1.6 |
| 9 | 12.0 | 7.6 | 29.0 | 3.4 | 7.0 | 4.2 | 3.0 | 2.6 | 1.5 |
| 10 | 7.0 | 5.1 | 25.5 | | | | | | |

(a)-(c) as in Examples 1-5.

EXAMPLES 11-15

From the reaction mixtures described in Examples 4 and 8-10, a solid reaction product was precipitated by cooling, the composition being p-DHP 65-75%, p-HHP 20-30%, and m-DHP 0-5%.

The precipitate was dissolved in methylisobutylketone (MIBK) to form approximately a 10% solution, with the hydroperoxides then being decomposed either with sulphuric acid or by using acid ion exchange resin (Amberlyst H+) to form corresponding phenols, as set forth in Table IV below, the decomposing temperature being 60° C. and the time, 20 min. The results were as reported in Table IV below.

TABLE IV

| Example (Sample) (a) | Decomos. catalyst | Starting material p-DHP % | Starting material m-DHP % | Product Hydroq., % Yield,% (b) | Res., % Yield,% (b) |
|---|---|---|---|---|---|
| 11 (4) | 0.15% $H_2SO_4$ | 4.26 | — | 2.08 (100.5%) | — |
| 12 (8) | 0.15% $H_2SO_4$ | 5.24 | — | 2.56 (100.8%) | — |
| 13 (9) | 0.15% $H_2SO_4$ | 4.65 | — | 2.27 (101.9%) | — |
| 14 (10) | 0.15% $H_2SO_4$ | 4.24 | 0.33 | 2.07 (100%) | 0.16 (99.5%) |

TABLE IV-continued

| Example (Sample) (a) | Decomos. catalyst | Starting p-DHP % | material m-DHP % | Product Hydroq., % Yield,% (b) | Res., % Yield,% (b) |
|---|---|---|---|---|---|
| 15 (10) | 4% Amberlyst | 4.24 | 0.33 | 2.01 (97%) | 0.15 (95%) |

(a) The precipitates obtained in Examples 4 and 8-10, dissolved in MiBK
(b) The yield has been calculated on the basis of the quantities of p-DHP and m-DHP from the result of analysis The preceding description of the present invention is merely exemplary, and is not intended to limit the scope thereof in any way.

We claim:

1. Method of producing hydroquinone which comprises
   oxidizing a mixture of about 10-80% by weight of diisopropylbenzene and about 20-90% by weight of $C_4$–$C_9$ alkylbenzenes by means of oxygen to form dihydroperoxide of p-diisopropylbenzene,
   cooling the thus-formed dihydroperoxide of p-diisopropylbenzene to crystalize the same, with other components of said thus-oxidized mixture remaining in solution, and
   separating the crystalized dihydroperoxide of p-diisopropylbenzene from the remaining components and decomposing the same by acid catalysis with at least one of mineral acid, acid aluminosilicate, sulphur trioxide, Lewis acid and acid ion exchange resin to form hydroquinone.

2. The method of claim 1, wherein the oxidizing of said reaction mixtur is carried out with the aid of oxygen and at a temperature of about 60°–180° C.

3. The method of claim 2, wherein said decomposing of the thus-separated dihydroperoxide of p-diisopropylbenzene is carried out at a temperature of about 20–150° C.

4. The method of claim 1, wherein said mixture which is oxidized comprises a by-product obtained in producing cumene and having a boiling range of about 170°–220° C.

5. The method of claim 1, wherein said remaining components comprise monohyroperoxides and dihydroperoxides of m-diisopropylbenzene remaining in solution.

6. The method of claim 1, wherein said decomposition of said dihydroperoxide of p-diisopropylbenzene additionally forms acetone.

7. The method of claim 1, wherein said mixture of $C_4$–$C_9$ alkylbenzenes comprises a mixture of t-butylbenzene, 1,1-dimethylpropylbenzene, i-hexylbenzene, 1-hexylbenzene, 2-phenylhexane, and 3-phenylhexane.

8. The method of claim 4, wherein said by-product comprises about 20–60% by weight of said $C_4$–$C_9$ alkylbenzenes.

9. The method of claim 2, wherein said oxidizing is carried out a temperature of about 90°–130° C.

10. The method of claim 1, wherein only tertiary aralkyl compounds present in said mixture are oxidized by said oxidizing thereof.

11. The method of claim 1, additionally comprising maintaining total hydroperoxide content in the oxidizing to about 10 to 80 weight percent.

12. The method of claim 11, wherein the total hydroperoxide content is maintained to about 20 to 60% by weight.

13. The method of claim 3, wherein said decomposing is carried out at a temperature of about 20°–120° C.

14. The method of claim 9, wherein said oxidizing is carried out at about a temperature of about 90°–100° C.

15. The method of claim 1, additionally comprising obtaining said mixture as a by-product of cumene production.

16. The method of claim 1, wherein said mineral acid includes sulfuric acid and phosphoric acid and said Lewis acid includes borotrifluoride and aluminum trifluoride.

17. The method of claim 1, additionally comprising
    removing any catalyst present in the thus-formed hydroquinone by filtering,
    whereby an extra acid-neutralizing step is avoided.

18. The method of claim 1, additionally comprising using a solvent in said decomposing which includes ketones, low-boiling aliphatic hydrocarbons, or low-boiling aromatic hydrocarbons.

19. The method of claim 18, wherein the ketones include acetone, methyl ethyl ketone, and methyl isobutyl ketone.

20. The method of claim 1, wherein
    only tertiary aralkyl compounds present in said mixture are oxidized by said oxidizing thereof, and
    of said thus-oxidized tertiary aralkyl compounds, only the dihydroperoxide of p-diisopropylbenzene is precipitated.

21. The method of claim 1, additionally comprising recycling said remaining components for oxidation.

22. The method of claim 21, wherein said remaining components are recycled at a ratio to said mixture of about 0.01:1 to about 10:1.

23. The method of claim 22, wherein said ratio is about 0.25:1 to about 2:1.

24. The method of claim 23, wherein said ratio is about 0.05:1 to about 2:1.

25. The method of claim 15, wherein said by-product comprises about 25% p-diisopropylbenzene, and about 50% of hydrocarbons acting as inert agents during said crystallizing.

26. The method of claim 1, wherein the remaining components act as inert diluent during the crystallizing of the dihydroperoxide of p-diisopropylbenzene, and thereby enhance the separation in crystalline form of the dihydroperoxide of p-diisopropylbenzene that is formed.

* * * * *